United States Patent
Rudel et al.

(10) Patent No.: US 9,726,683 B2
(45) Date of Patent: Aug. 8, 2017

(54) METHODS FOR PREDICTING RISK OF CORONARY STENOSIS

(71) Applicant: Wake Forest University Health Sciences, Winston-Salem, NC (US)

(72) Inventors: Lawrence L. Rudel, Winston-Salem, NC (US); Chadwick D. Miller, Stokesdale, NC (US); Michael J. Thomas, Pfafftown, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/948,938

(22) Filed: Nov. 23, 2015

(65) Prior Publication Data

US 2016/0169922 A1  Jun. 16, 2016

Related U.S. Application Data (62) Division of application No. 14/119,345, filed as application No. PCT/US2012/039999 on May 30, 2012, now Pat. No. 9,222,948.

(60) Provisional application No. 61/492,083, filed on Jun. 1, 2011.

(51) Int. Cl.
  *G01N 33/92* (2006.01)
  *G06F 19/00* (2011.01)

(52) U.S. Cl.
  CPC ......... *G01N 33/92* (2013.01); *G06F 19/3431* (2013.01); *G01N 2405/00* (2013.01); *G01N 2560/00* (2013.01); *G01N 2800/323* (2013.01); *G01N 2800/50* (2013.01); *G01N 2800/56* (2013.01)

(58) Field of Classification Search
  None
  See application file for complete search history.

(56) References Cited

U.S. PATENT DOCUMENTS

| | | | |
|---|---|---|---|
| 5,756,067 A | 5/1998 | Redgrave et al. | |
| 7,939,287 B2 | 5/2011 | Tsimikas et al. | |
| 7,973,023 B2 * | 7/2011 | Harats | A61K 31/075 514/114 |
| 9,222,948 B2 * | 12/2015 | Rudel | G01N 33/92 |
| 2003/0109442 A1 | 6/2003 | Bisgaier et al. | |
| 2009/0226420 A1 | 9/2009 | Hauser et al. | |
| 2010/0173346 A1 * | 7/2010 | Adourian | G01N 33/6893 435/29 |
| 2010/0291688 A1 | 11/2010 | Lu et al. | |
| 2011/0008805 A1 * | 1/2011 | Urdea | G01N 33/74 435/7.92 |

OTHER PUBLICATIONS

Bondjers G. et al. Aortic Intimal Lipid Content and Serum Lipoproteins in Patients Undergoing Coronary by Pass Surgery as Related to Clinical Prognosis. Atherosclerosis 72(2-3)231-239, Aug. 1988.*
International Search Report and Written Opinion, PCT/US2012/039999, mailed Nov. 19, 2012.
Ismaiel OA et al. Investigation of endogenous blood plasma phospholipids, cholesterol and glycerides that contributed to matrix effects in bioanalysis by liquid chromatography/mass spectrometry. Journal of Chromatography B. 2010; 878: 3303-3316.
Blanksby SJ and Mitchell TW. Advances in mass spectrometry for lipidomics. Annual Review Analytical Chemistry. 2010; 3: 433-65.
Fuchs B and Schiller J. Application of MALDI-TOF mass spectrometry in lipidomics. Eur. J. Lipid Sci. Technol. 2009; 111: 83-98.
Bleijerveld OB et al. Metabolipidomics: profiling metabolism of glycerophospholipid species by stable isotopic precursors and tandem mass spectrometry.
Curcio CA et al. A local source for esterified cholesterol (EC) in human Bruch's membrane (BrM). Investigative Ophthalmology & Visual Science. 2002; 43: E-Abstract 862.

* cited by examiner

*Primary Examiner* — Ralph Gitomer
(74) *Attorney, Agent, or Firm* — Myers Bigel, P.A.

(57) ABSTRACT

A computer-based method for determining a prediction of risk and/or an indication of extent of coronary stenosis in a human subject, comprises the steps of: (a) inputting the level of at least one cholesteryl ester measured in a blood sample collected from said subject; and then (b) inputting the age and gender of said subject; and then (c) generating in said computer from said cholesteryl ester level input, said age input and said gender input a prediction of risk and/or an indication of extent of coronary stenosis in said subject. Systems and methods are also described.

22 Claims, 3 Drawing Sheets

Figure 1: Schematic Diagram of a System Embodiment

Figure 2. CE values by the presence of significant coronary stenosis

Figure 3. Receiver operator characteristic curves for full and reduced models to predict CAD.

METHODS FOR PREDICTING RISK OF CORONARY STENOSIS

RELATED APPLICATIONS

This application is a divisional of and claims priority to U.S. patent application Ser. No. 14/119,345, filed Jan. 30, 2014, U.S. Pat. No. 9,222,948, which is a 35 U.S.C. §371 national phase entry of PCT Application PCT/US2012/039999, filed May 30, 2012, and published in English on Dec. 6, 2012, as International Publication No. WO 2012/166798, and which claims the benefit of U.S. Provisional Patent Application Ser. No. 61/492,083, filed Jun. 1, 2011, the disclosure of each of which is incorporated herein by reference in its entirety.

FIELD OF THE INVENTION

The present invention is directed to methods for determining a prediction of risk and/or indication of extent of coronary stenosis or atherosclerosis in human subjects using cholesteryl ester levels.

BACKGROUND OF THE INVENTION

Annually in the US, 6 million patients present to emergency departments with acute chest pain or related complaints. (1) Most patients with acute chest pain presenting to emergency departments undergo an evaluation for possible acute coronary syndrome (ACS), yet the vast majority does not have this disease process. After exclusion of myocardial infarction (MI) with serial cardiac necrosis biomarkers, practice guidelines recommend further evaluation of patients with possible ACS with stress testing or coronary CT angiography (CCTA). (2) This practice is currently necessary to prevent the discharge of patients with unstable angina, but leads to a large number of negative tests. A biomarker is needed to predict patients likely to have underlying coronary artery disease (CAD) among patients with acute chest pain. A biomarker better able to identify patients likely to have coronary disease could improve testing efficiency by either reducing pretest probability below the testing threshold, or by guiding selection of the cardiac imaging modality.

Traditional cardiac risk factors, such as smoking, diabetes, and hypercholesterolemia, have been shown to correlate strongly with the long-term risk of developing coronary atherosclerosis. (3-5) In patients with acute chest pain, these risk factors have been shown to be only weak predictors of cardiac chest pain. (6) The rationale for this apparent discrepancy relates to the importance of the clinical history and the presence of acute chest pain being a much stronger relative predictor for symptomatic disease than these traditional risk factors.

SUMMARY OF THE INVENTION

The present invention provides systems and methods for determining a prediction of risk and/or an indication of extent of coronary stenosis in a human subject. The method comprises the steps of: providing or inputting a level of at least one cholesteryl ester measured (e.g., by mass spectroscopy) in a blood sample collected from the subject; and then determining from the cholesteryl ester level a prediction of risk and/or indication of extent of coronary stenosis in the subject.

In some embodiments, the method further comprises the step of: providing the age and/or gender of the subject; and wherein the determining step includes determining a prediction of risk and/or indication of extent of coronary stenosis in the subject from the cholesteryl ester level, along with the age and/or gender of the subject.

In some embodiments, the subject is afflicted with acute chest pain (angina) or other symptom of acute coronary syndrome; in some embodiments, the coronary stenosis is significant coronary stenosis.

In some embodiments, the subject is not afflicted with acute chest pain or other symptom of acute coronary syndrome; in some embodiments, the coronary stenosis is moderate coronary stenosis.

In some embodiments, the cholesteryl ester comprises, consists of or consists essentially of CE 16:1 and CE 18:1 in combination.

Recently, acyl-CoA:cholesterol acyltransferase-2 (ACAT2) activity has been shown in monkey and murine models to correlate with atherosclerosis. (7-9) Hepatic ACAT2 is the primary source of cholesteryl ester (CE) produced from the monounsaturated fatty acids palmitoleic acid (16:1) and oleic acid (18:1) and has also been associated with CE produced from palmitic acid (16:0). Higher plasma concentrations of these CE have been linked to increased risk for MI in a longitudinal cohort of men followed over 19 years. (10) Whether measurement of these CE in plasma may be informative to care providers when assessing patients with acute chest pain has heretofore been unclear.

The foregoing and other objects and aspects of the present invention are explained in greater detail in the drawings herein and the specification set forth below.

DETAILED DESCRIPTION OF THE EMBODIMENTS

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety.

Also as used herein, "and/or" refers to and encompasses any and all possible combinations of one or more of the associated listed items, as well as the lack of combinations when interpreted in the alternative ("or").

The present invention may be embodied as systems, methods, and/or computer program products. Accordingly, the present invention may be embodied in hardware and/or in software (including firmware, resident software, microcode, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any non-transient medium that can contain or store the program for use by or in connection with the instruction execution system, apparatus, or device.

The computer-usable or computer-readable medium may be, for example but not limited to, an electronic, magnetic, electromagnetic, infrared, or semiconductor system, apparatus, or device. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), and a portable compact disc read-only memory (CD-ROM).

1. Definitions

"Cholesteryl ester" as used herein refers to an ester of cholesterol and one or more fatty acids. The ester bond is formed between the carboxylate group of the fatty acid and the hydroxyl group of cholesterol. Examples of particular cholesteryl esters that may be measured to carry out the present invention include, but are not limited to, cholesteryl myristate (CE 14:0), cholesteryl palmitate (CE 16:0), cholesteryl palmitoleate (CE 16:1), cholesteryl heptadecenoate (CE 17:1), cholesteryl stearate (CE 18:0), cholesteryl oleate (CE 18:1), cholesteryl linoleate (CE 18:2), cholesteryl linolenate (CE 18:3) (including cholesteryl alpha-linolenate (CE 18:3n-3) and cholesteryl gamma-linolenate (CE 18:3n-6)), cholesteryl arachidonate (CE 20:4), cholesteryl eicosatrienoate (CE 20:3), cholesteryl eicosapentaenoate (CE 20:5), cholesteryl docosapentaenoate (CE 22:5), cholesteryl docosahexaenoate (CE 22:6), and combinations thereof (including any combination of 2, 3, or 4 or more thereof).

"Risk of coronary stenosis" as used herein is different from "extent of coronary stenosis" as discussed below, and is intended to convey a probability that a subject is afflicted with coronary stenosis sufficient to warrant further diagnostic, preventative, therapeutic, and/or interventional medical attention. Risk may be conveyed in a variety of ways, including but not limited to: a scale such as 1 to 10; as a risk category (low vs. moderate vs. high), as a binary classification (at risk vs. not at risk), as a percent likelihood). If desired, the indication of risk may further comprise, or be in the form of, an indication of extent of coronary stenosis in the subject.

"Extent of coronary stenosis" refers to the severity of coronary stenosis and/or the burden of coronary atherosclerosis and as used herein may be indicated in any suitable manner. The indication may be given as a verbal or text explanation (e.g., serious coronary stenosis, versus significant coronary stenosis, versus moderate coronary stenosis, versus minor coronary stenosis, or any combination or subcombination thereof) with suitable definitions of terms as necessary. The indication may be given as a range (e.g., a scale of 1 to 5 or 10, with 1 indicating little stenosis and 5 or 10 indicating severe stenosis), as a percentage of occlusion (including ranges thereof), as a color warning in a visual display (e.g., green, for little or no stenosis, yellow for moderate coronary stenosis; red for significant coronary stenosis), and/or by any other suitable technique.

"Significant coronary stenosis" as used herein refers to a blockage of fifty percent or more of a named coronary artery (for example, the right coronary artery, the posterior descending artery, the right marginal artery, the left coronary artery, the left circumflex artery, the left marginal artery, and the left anterior descending artery (including the diagonal branch).

"Moderate coronary stenosis" as used herein refers to detectable coronary stenosis in any coronary artery, but with less than a fifty percent blockage of any named coronary artery.

"Blood sample" as used herein may be any suitable blood sample, including blood plasma, blood serum, and whole blood.

"Risk factor" or "additional risk factor" as used herein includes, but is not limited to, hyperlipidemia, smoking, diabetes, hypertension, obesity, substance abuse (e.g., alcohol abuse or alcoholism), sedentary lifestyle or lack of exercise, family history including race (e.g., one or more parent with heart disease), etc. Age (e.g., over 65) and gender (particularly male gender) may be considered risk factors as well, but are addressed separately herein.

"Subject" as used herein are human subjects of any race and gender. While the subjects may be of any age, including juvenile and adolescent subjects, typical subjects are adult and geriatric subjects. Subjects may be with, or without, chest pain (angina) or other symptoms of acute coronary syndrome.

"Symptoms of acute coronary syndrome" include, but are not limited to: chest pain (angina), particularly chest pain that feels like burning, pressure, or tightness and lasts several minutes or longer; pain elsewhere in the body such as the left upper arm or jaw; nausea; vomiting; shortness of breath; sudden, heavy sweating, etc.

2. Elements of the Invention

The present invention can be carried out by any suitable technique. Whole blood can be collected from a subject, processed if desired into blood serum or plasma, and further prepared for measurement of cholesteryl esters therein by any suitable technique, including known techniques or the mass spectrometry techniques described below. Once a measurement of cholesteryl esters in a patient sample is obtained, an indication of risk and/or extent of coronary stenosis can be determined by reference to a table or tables generated by the data and/or techniques described herein. Separate tables and/or table entries can be provided based on the subject's age and/or gender, and the presence or absence of other risk factors (such as those discussed below) if desired.

Figure 1:
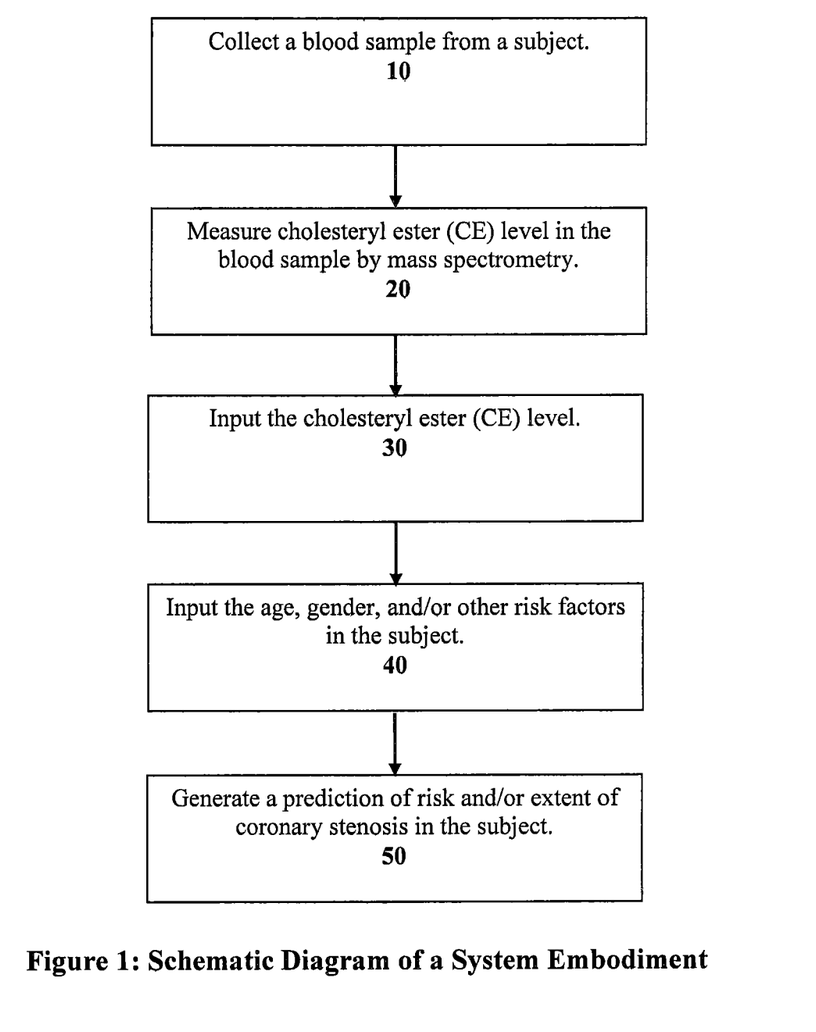
FIG. 1. Schematic diagram of a non-limiting example of a system and method of the invention.

In some embodiments, the invention may be carried out as a computer-based method for determining a prediction of risk and/or an indication of extent of coronary stenosis in a human subject, as illustrated in FIG. 1. Such methods typically comprise: (a) inputting the level of at least one cholesteryl ester measured in a blood sample collected from the subject; (b) inputting the age and gender of the subject (which can be done before or after inputting step (a)); and then (c) generating from the cholesteryl ester level, the age and the gender a prediction of risk and/or an indication of extent of coronary stenosis in the subject. The generating step may be carried out by any suitable technique, such as with a regression model or an empirically-based model of actual clinical experience.

In some embodiments, the method may further comprise inputting the presence or absence of at least one additional risk factor (and in some embodiments 2 or 3 or more additional risk factors) in the subject. Hence, the generating step further comprises generating from the cholesteryl ester level, the age, and the at least one additional risk factor a prediction of risk and/or indication of extent of coronary stenosis in the subject.

In some embodiments, such as where the subject is afflicted with acute chest pain or other indication of acute coronary syndrome, the indication of coronary stenosis can be an indication of significant coronary stenosis. In other embodiments, such as where the subject is not afflicted with acute chest pain or other indication of acute coronary syndrome, the indication of coronary stenosis may be an indication of moderate coronary stenosis.

In some embodiments, the cholesteryl ester measured comprises, consists of or consists essentially of CE 16:1 and CE 18:1, in combination (e.g., the sum of the two thereof).

3. Mass Spectroscopy

The level of the at least one cholesteryl ester in the blood sample can be determined by any suitable means, but in some embodiments is preferably determined by mass spectrometry.

Thus, the present invention provides a method of measuring the amount of at least one cholesteryl ester in a blood sample by mass spectrometry. The method comprises:

combining (in any convenient sequence or order and at any suitable temperature such as room temperature) the blood sample with a salt and a diluents such as an alcohol (and optionally other diluents or ingredients such as water, buffering agents, etc.) to provide a dilute sample;

introducing the dilute sample into a mass spectrometer (e.g., by directly introducing the sample into the mass spectrometer, typically by introducing or injecting a volume of from 0.1 or 1 to 100 or 500 microliters thereof); and then measuring the amount of the at least one cholesteryl ester in the dilute sample by mass spectrometry (i.e., in the mass spectrometer into which the sample has been introduced) to thereby measure (and quantify) the amount of at least one cholesteryl ester in the blood sample.

If desired, an additional known cholesteryl ester (typically different from the CE's being measured) may be added to the dilute sample in a known amount as an internal standard. While particular conditions for performing the steps, such as times and temperatures, are not critical, in some preferred embodiments, all of the steps are carried out within a relatively short period of time: e.g., within 24 hours, within 8 hours, or in some embodiments in 2 hours or less.

In some embodiments, the diluent is provided in an amount sufficient to achieve at least a 50, 100 or 200-fold (by volume) dilution of the blood sample, up to a 1000 or 2000-fold dilution (or more). For example, in some embodiments, the blood sample is included in the diluents in an amount ranging from 0.01 percent by volume, up to 1, 2, or 10 percent by volume. Suitable alcohols for use as diluents include, but are not limited to, methanol, ethanol, and isopropanol. Without wishing to be limited to any theory of the invention, the diluent may be included in an amount sufficient to solubilize the at least one cholesteryl ester in the sample.

In some embodiments, the salt is added in an amount of from 0.001 or 0.01 mg to 1 or 10 mg of the salt in the dilute sample. Suitable salts include, but are not limited to, sodium formate, sodium acetate, ammonium formate, ammonium acetate, lithium formate, lithium acetate, potassium formate, potassium acetate, and other alkali metal salts of fatty acids. Without wishing to be limited to any theory of the invention, the salt may be included in an amount sufficient to form a metal adduct with the cholesteryl ester in the sample.

Suitable equipment for carrying out mass spectrometry is known and specific techniques for carrying out the methods of the invention can be carried out in accordance with known procedures or variations thereof that will be apparent to those skilled in the art. See, e.g., E. de Hoffman and V. Stroobant, *Mass Spectrometry: Principles and Applications* (3d ed. 2007).

The present invention is explained in greater detail in the non-limiting examples set forth below.

EXPERIMENTAL

The objective of this study is to test whether there is potential diagnostic value in measuring plasma levels of ACAT2 associated CEs when evaluating patients with possible ACS. This investigation examines whether there is any association between measured CE levels and any definable coronary stenosis, or significant coronary stenosis, measured at angiography. The premise is that a more accurate estimate of a patient's likelihood of having CAD, when presenting with acute chest pain, will improve healthcare delivery by allowing more judicious use of diagnostic tests.

I. Methods.

Study Design.

The study, a single site observational cohort, was approved by the institutional review board of the Wake Forest University School of Medicine and all participants provided written informed consent.

Study Setting and Population.

The study population consisted of patients at the study institution who were at least 18 years old undergoing angiography of the coronary arteries with either cardiac catheterization or computed tomography. The overall goal of the study was to assemble a repository for the testing of novel cardiac biomarkers; therefore, only patients with inability to follow up or anemia (hemoglobin<8.0) were excluded. The observational cohort consisted of two distinct patient populations from Wake Forest University Baptist Medical Center, patients referred for invasive coronary angiography, and patients undergoing coronary computed tomographic angiography (CCTA) in the observation unit of the emergency department. The analysis of plasma CE composition to use as a biomarker was the a priori primary analysis from this cohort.

This analysis includes patients enrolled from either the ED or the hospital setting and further required that the patients had chest pain or related symptoms. The ED population consists of patients who presented with chest pain or related complaints, received a primary assessment, and the care providers felt them be at low risk for ACS based on initial cardiac biomarkers and the initial electrocardiogram. After the primary assessment, the patients were placed in the ED observation unit, had a CCTA ordered, and were then approached for enrollment. The basis for the clinical assessment was an overall impression of low risk based on the framework set forth in the ACC/AHA guidelines (11) and a Thrombolysis in Myocardial Infarction (TIMI) risk score (12) of 0 or 1 correlating to a short term risk for ACS of 2-5% (13). Patients recruited from the hospital setting were patients with and without known ACS being referred to angiography for either definition of coronary anatomy or coronary intervention.

Study Procedures.

After obtaining informed consent, participants underwent a single blood draw, provided background information about their history and demographics, and completed a food frequency questionnaire. The food frequency questionnaire administered was the Block Brief 2000 (NutritionQuest, Berkeley, Calif.), chosen for both its brevity and the ability to quantify monounsaturated, polyunsaturated, and saturated fat intake. Clinical outcomes at 30 days were assessed using a scripted telephone interview and a structured medical record review. The primary investigator reviewed all case report forms to make a final determination of ACS during the index hospital visit and at 30 days based on an objective study definition and blinded to CE measurements. Clinical data collection was consistent with standardized guidelines for ED patients with possible ACS. (14)

Coronary Imaging.

Participants undergoing coronary angiography had findings abstracted from the clinical reports. Invasive angiography was performed using conventional techniques and the most severe diameter stenosis was recorded on the case report form for each reported vessel. Participants with prior bypass grafts had stenoses recorded for both native and graft vessels. Methods used at the study institution to assess the coronary vasculature with CCTA have been previously described (ref in press). In brief, all participants underwent coronary imaging with a 64-slice LightSpeed VCT (GE Healthcare, Milwaukee, Wis.). Most patients first received oral and/or IV beta-blockade. Initial scout images were obtained followed by a low-dose, noncontrast, ECG-gated acquisition for calcium scoring. The subsequent contrast injection was a triple-phase intravenous injection consisting of 100 mL of nonionic iodinated contrast (Optiray 350; Mallinckrodt Medical, Hazelwood, Mo.) followed by an ECG-gated acquisition. Raw image data was then used to create multiphase images that were post-processed and analyzed on an independent 3D workstation (Advantage Workstation 4.2, GE Healthcare). Image interpretation occurred as part of clinical care. Interpreting radiologists and cardiologists meeting level 2 or 3 training guidelines from the ACC/AHA for cardiac CT. (15) Coronary stenosis was measured using an electronic caliper and comparing the average luminal diameter in the most stenotic region with the average luminal diameter of a normal proximal or distal reference segment located within 1 cm of the stenosis without intervening branch vessels.

Data Handling and Follow Up.

Sources of data included the participants, care providers, and the medical record. Data templates were used to collect data directly from the patient and care providers for data fields that were anticipated to be unreliable in the medical record. Abstraction of medical record data was guided by a "sources of data" document describing the expected location and definition of each data field. Data from paper case report forms were then entered into a web-based electronic database.

Sample Acquisition and Processing.

Whole blood was collected via venipuncture into vacutainer tubes containing EDTA. Cells were separated from plasma by centrifugation at a minimum of 1700 RPM for 15 min in a tabletop centrifuge at 4° C. Plasma was subsequently aspirated from the cell layer. Plasma was stored at −70° C. until analysis was done. Lipoprotein cholesterol distributions were determined on whole plasma using size separations via gel filtration chromatography, similar to the method of Garber, et al. (16) Plasma (containing about 15 μg of cholesterol) diluted 1:1 with cold phosphate buffered saline was applied to a Superose 6 column (GE Healthcare). The column is eluted with 0.9% saline containing 0.01% EDTA and 0.01% sodium azide at a flow rate of 0.4 ml/min using a LaChromElite HPLC system (Hitachi High Technologies) and the column eluate is continuously mixed online with 0.125 ml/min cholesterol reagent (Cholesterol Liquid Reagent Set, Pointe Scientific, Inc) that is then passed through a 5 mL knitted reaction coil maintained at 37° C. Data readout is proportional to cholesterol concentration in the eluate, and fractions containing VLDL, LDL and HDL are identified so that the percentage of cholesterol in each can be determined. The concentrations in each lipoprotein class are then calculated from a direct measure of cholesterol concentration in an aliquot of the starting plasma. The measurement of cholesterol and triglyceride concentrations in whole plasma was done using enzymatic methods for cholesterol(17) and triglycerides(18).

Mass spectrometry was used for measurement of CEs. Samples were stored at −70° C. before analysis. After thawing, 5 μL of plasma was added to 1 mL methanol solution containing 5 ng/μL 17:0 CE (internal standard) and 10 ng/μL sodium formate. The solution was vortexed for 10 seconds and then allowed to stand at room temperature for 30 minutes. 100 μL of the first solution was diluted 1:10 with high purity methanol. Individual CEs were measured using a Quattro II mass spectrometer equipped with a Z-spray interface. Analysis parameters were as follows: capillary voltage=3.2 kV, cone voltage=50V, source temperature=80° C., and desolvation temperature=200° C. Samples were maintained at 15° C. in a temperature controlled Spark Holland Reliance autosampler/stacker while awaiting analysis. 25 μL of each sample was infused into the mass spectrometer at 10 μL/min. CE were quantified in the positive ion mode by monitoring the common neutral loss of 368.4 Da. The CE profile and quantitation were calculated from this data and presented in an electronic spreadsheet. Cholesteryl esters measured included those with the following fatty acids: palmitate, 16:0; palmitoleate, 16:1; stearate, 18:0; oleate, 18:1; linoleate, 18:2; linolenate, 18:3; arachidonate, 20:4; eicosapentenoate, 20:5; and docosahexanoate, 22:6. Measurements were reported in percentages of total CE by mass and plasma concentrations ($10^{-3}$ mol/m$^3$) of each, and both measures were examined in the data analysis.

Primary Outcomes.

The primary outcome was the presence of CAD, measured either by CCTA or invasive angiography. Severity of the maximal diameter of stenosis was recorded and the patients were dichotomized as a) positive or negative for CAD, and b) positive or negative for significant CAD (≥50%). Ranges of stenosis were recorded as the highest value of the range. Stenosis caused by myocardial bridging alone was not included in this analysis.

Sample Size.

Variance and effect size data for this novel biomarker were not available in humans. At the outset it was empirically estimated that approximately 100 participants with varying degrees of CAD would provide at least preliminary evidence of a clinically important relationship, if one existed. It was estimated that this would provide sufficient event rates of coronary stenosis to satisfactorily fit exploratory multiple variable logistic regression models, considering the standard "rule of ten" recommending ten events for every degree of freedom considered in the multivariate model.[26]

Data Analysis.

The first objective was to determine if there was an association between measured CE levels and coronary stenosis. Two definitions of coronary stenosis were examined, any measurable CAD and significant (>50%) stenosis. Means and standard deviations, medians with inter-quartile ranges, and proportions were used to describe normally distributed continuous variables, skewed continuous variables and categorical variables, respectively. Cholesterol esters related to ACAT2 (16:0, 16:1, and 18:1) and their sums were examined among participants with and without coronary stenosis and compared with Kruskal-Wallis tests. Cholesteryl palmitate concentrations contributed in a different direction than cholesteryl palmitoleate and cholesteryl oleate. Mechanistically, ACAT2 is directly involved in the synthesis of the latter two cholesteryl esters after the activity of steroyl CoA desaturase 1 to introduce the double bond, whereas the synthesis of cholesteryl palmitate does not require prior steroyl CoA desaturase 1 activity. Therefore this CE was removed and the sum of 16:1 and 18:1 were further examined.

Logistic regression was used to assess the relationship between the sum of cholesteryl palmitoleate plus cholesteryl oleate and coronary stenosis. Separate models using absolute CE concentrations, mass percentages, and both CAD endpoints (any stenosis, >50% stenosis) were constructed. Univariate logistic regression was performed between potential covariates and the endpoint under consideration, and those covariates with a Wald p<0.20 were then considered for inclusion in the multivariate model. Covariates included age, dietary intake of monounsaturated and polyunsaturated fat, gender, total plasma cholesterol, LDL, HDL, body mass index, and a summary measure of traditional coronary risk factors (smoking, diabetes, hypertension, dyslipidemia) ranging from zero to four. Graphic examination and fractional polynomial analysis(19) indicated that continuous variables were best treated as linear within the models. Model construction was performed manually beginning with the full model with backward removal of covariates in order to build a parsimonious model. The CE term was retained at all steps; a Wald p<0.05 was required for other covariates to be retained within the model. Interaction terms were generated via the product method and assessed for inclusion, as were covariates with the potential to be effect modifiers of the relationship between the CE and endpoint. Additional models were generated to assess these relationships within the low risk ED subgroup with acute chest pain. An additional set of models examined the sum of CE concentrations (16:1, 18:1, 18:3, 20:4, 20:5, and 22:6) as the primary predictor covariate against the outcomes of any stenosis and significant stenosis. Given the exploratory nature of this analysis, we made no adjustment to any p values for the construction of multiple models. The Hosmer-Lemeshow goodness of fit test was used to assess model fit, and receiver area operating curves were generated to produce a c-statistic. Contributions of CE were assessed between the final full model and a reduced model without the CE by comparison of the receiver operator characteristic (ROC) curve C statistic, and integrated discrimination improvement (IDI). The IDI is a measure of the discriminatory ability of the models with and without the marker of interest. Each model was assessed for outliers and overly influential points utilizing Pregibon's dbeta statistic. Additional models were generated to assess these relationships within the low risk ED subgroup with acute chest pain. An additional set of models examined the sum of CE concentrations (16:1, 18:1, 18:3, 20:4, 20:5, and 22:6) as the primary predictor covariate against the outcomes of any stenosis and significant stenosis.

The secondary objective was to examine the potential effect of the resulting final model in the subgroup of ED patients with low risk chest pain. This was first accomplished by comparing the final model with the Diamond and Forrester classification using the IDI. The final model was also then applied to the low risk subgroup to determine the potential reduction in imaging and the resulting missed ACS rate at 30 days. Data analysis was conducted with SAS Enterprise Guide, v4.2 (SAS Institute Inc., Cary, N.C.) and Stata/IC 11.2 (College Station, Tex.).

II. Results

The observational cohort consisted of 150 participants enrolled over 24 months at the time of this analysis. Of these 150, 37 participants were excluded for meeting one or more of the following exclusions: no available blood samples (n=10), no coronary imaging (n=7), no food frequency questionnaire data (n=21), and no acute chest pain (n=3). The final dataset for this analysis consisted of 113 participants with complete data; 58% were enrolled from the observation unit and 42% were enrolled from the angiography suite.

Participants were a mean age of 49 (+/−11.7) years, 38% were women (Table 1). Conventional coronary risk factors among study participants included hypertension (43%), current smoking (37%), diabetes (19%), hyperlipidemia (42%), history of cocaine use (16%), and 16% of the study population had experienced a prior MI. Most participants had a chief complaint of chest pain (91%) and a normal (53%) or nonspecific ECG (28%) nearest to enrollment. During the index visit, 23% had experienced MI and 26% had received revascularization (Table 2).

TABLE 1

Participant Demographics and Past Medical History

| Patient Characteristics | No CAD n/N (%) | CAD n/N (%) |
|---|---|---|
| Age (years)* | 40.9 (8.6) | 55.0 (10.0) |
| Female sex | 23/46 (50.0) | 20/67 (29.9) |
| White race | 28/46 (60.9) | 53/67 (79.1) |
| Hypertension | 12/46 (26.1) | 36/67 (53.7) |
| Diabetes mellitus | 4/46 (8.7) | 17/67 (25.4) |
| Current smoking | 17 (37.0) | 25/67 (37.3) |
| History of cocaine use | 8/46 (17.4) | 10/67 (14.9) |
| Hyperlipidemia (by history) | 9/46 (19.6) | 38/67 (56.7) |
| Body Mass Index* | 29.7 (5.8) | 29.8 (5.8) |
| Prior Heart Failure | 0/46 (0) | 3/67 (4.5) |
| Prior myocardial infarction | 1/46 (2.2) | 17/67 (25.4) |

*= data presented as mean(SD);
CABG = Coronary artery bypass graft;

TABLE 2

Presenting Characteristics and Physical Exam Findings

| | No CAD n/N (%) | CAD n/N (%) |
|---|---|---|
| Presenting Characteristics | | |
| Chest pain chief complaint | 39/44 (88.6) | 61/66 (92.4) |
| Chest pain at rest | 36/43 (83.7) | 45/65 (69.2) |
| Multiple episodes of symptoms within 24 hours of presentation | 15/43 (34.9) | 29/64 (45.3) |
| Chest pain pleuritic | 8/43 (18.6) | 12/63 (19.0) |
| Physical Exam | | |
| Heart rate (beats/minute)* | 78.9 (14.4) | 68.9 (23.1) |
| Systolic blood pressure (mmHg)* | 136.6 (35.4) | 131.3 (31.6) |
| Murmur | 1/42 (2.4) | 6/65 (9.2) |
| Rales | 0/44 (0) | 6/65 (9.2) |
| Jugular venous distention | 0/43 (0) | 0/65 (0) |
| Overall electrocardiogram classification | | |
| Normal | 30/46 (65.2) | 30/67 (44.8) |
| Nonspecific changes | 13/46 (28.3) | 19/67 (28.4) |
| Early repolarization only | 0/46 (0) | 2/67 (3.0) |
| Abnormal but not diagnostic of ischemia | 1/46 (2.2) | 2/67 (3.0) |
| Infarction or ischemia known to be old | 0 (0) | 4/67 (6.0) |
| Infarction or ischemia not known to be old | 1/46 (2.2) | 7/67 (10.5) |
| Suggestive of myocardial infarction | 1/46 (2.2) | 3/67 (4.5) |
| Risk Stratification TIMI risk score | | |
| 0 | 25/46 (54.4) | 12/67 (17.9) |
| 1 | 17/46 (37.0) | 16/67 (23.9) |
| 2 | 3/46 (6.5) | 11/67 (16.4) |
| 3 | 1/46 (2.2) | 15/67 (22.4) |
| 4 | 0/46 (0) | 10/67 (14.9) |
| 5 | 0/46 (0) | 2/67 (3.0) |
| 6 | 0/46 (0) | 1/67 (1.5) |
| 30-day acute coronary syndrome | 1/46 (2.2) | 35/67 (52.2) |
| Cardiovascular death | 0/46 (0) | 1/67 (1.5) |
| Myocardial infarction | 1/46 (2.2) | 25/67 (37.3) |
| Revascularization | 0/46 (0) | 29/67 (43.3) |

*= data presented as mean(SD);
TIMI = thrombolysis in myocardial infarction

Computed tomography coronary angiography was the diagnostic standard for coronary imaging in 56% of participants with the remainder undergoing invasive angiography. At angiography, 59% had coronary stenosis and 43% had significant coronary stenosis in at least 1 named coronary artery. Two participants undergoing CCTA had major coronary segments that could not be quantified due to artifact and were classified based on the available information. As a measure of disease burden, coronary artery disease severity scores(20) were calculated among participants with significant coronary stenosis for each main coronary vessel (excluding the 2 participants with incomplete data for this calculation). Among these participants, the severity score averaged across all 4 main coronary vessels (including left main) was 4.3 (+/−6.1). At least 50% stenosis was seen in 1, 2, 3, and 4 coronary distributions in 17, 11, 9, and 1 participants, respectively.

Figure 2:
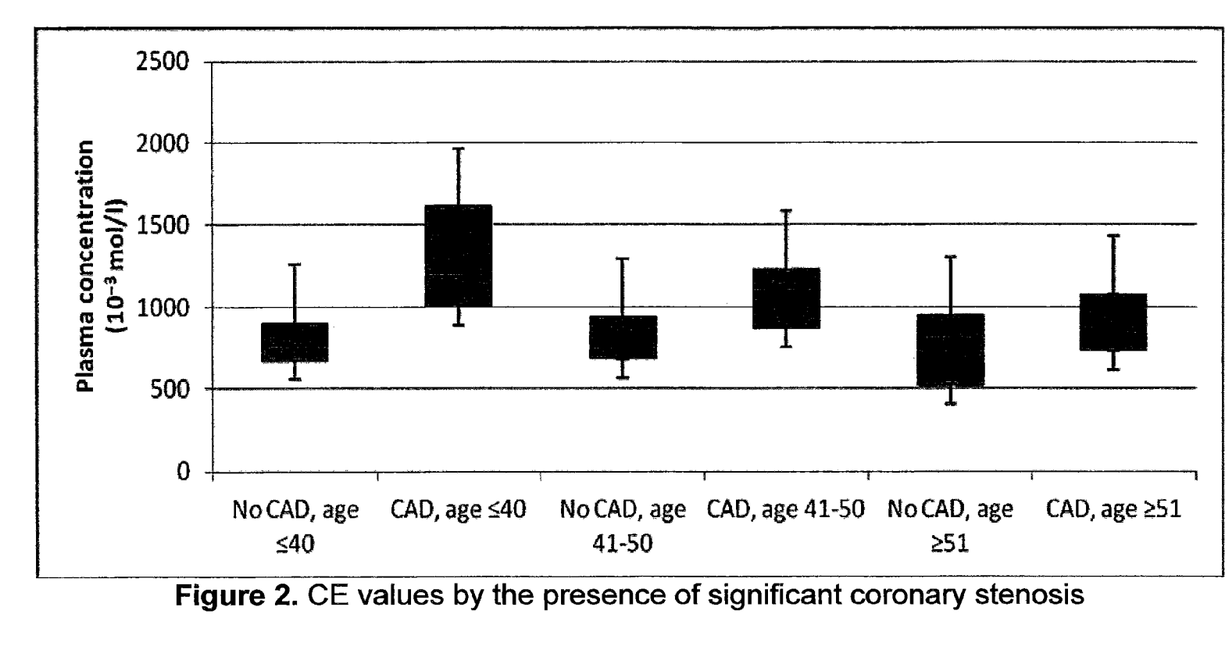
FIG. 2. CE values by the presence of significant coronary stenosis. The boxplots represent the values of the sum of cholesteryl esters 16:1 and 18:1 measured in participants. The box margins represent the $25^{th}$ and $75^{th}$ percentiles, the bar within the box represents the median, and the whiskers represent the range of values.

Stratifying the cohort into participants with and without CAD, dietary fat intake and plasma lipid concentrations were similar between groups (Table 3). Cholesteryl ester concentrations were significantly higher for 16:1, 18:1, 18:3, 20:4, 20:5, and 22:6 among participants with coronary stenosis (Table 4, FIG. 2). Based on the study hypothesis, the sum CE (16:1 and 18:1) was of primary interest and was significantly higher in both mass percent and concentration in those with CAD. FIG. 2 suggests that sum CE (16:1 and 18:1) may be more useful in patients 40 years old or younger. This subgroup consisted of 29 participants, 6 with any CAD.

TABLE 3

Dietary intake, serum and plasma results

| | No CAD Mean (SD) | CAD Mean (SD) | p value |
|---|---|---|---|
| Dietary intake (daily estimated intake) | | | |
| Total fat (g) | 79.8 (39.2) | 81.3 (51.2) | 0.86 |
| Saturated fat (g) | 26.5 (13.2) | 26.4 (17.2) | 0.96 |
| Monounsaturated fat (g) | 31.0 (16.1) | 31.6 (19.6) | 0.86 |
| Polyunsaturated fat (g) | 16.0 (7.8) | 17.1 (11.7) | 0.54 |
| Dietary cholesterol (g) | 235.7 (137.2) | 257.0 (203.3) | 0.51 |
| Olive oil use for cooking, n/N (%) | 23/46 (50.0) | 30/67 (44.8) | 0.70† |
| Plasma lipids (mg/dl) | | | |
| Total cholesterol | 166.6 (27.5) | 178.7 (44.6) | 0.0780 |
| VLDL | 19.7 (12.1) | 23.8 (14.5) | 0.1237 |
| LDL | 105.0 (21.0) | 113.7 (36.0) | 0.1094 |
| HDL | 41.9 (13.1) | 41.3 (16.2) | 0.83 |

Comparisons were conducted using t-tests.
VLDL = very low density lipoprotein;
LDL = low density lipoprotein;
HDL = high density lipoprotein;
For all analyses, p <= .05 denotes statistical significance, with no adjustment for the multiple comparisons.

TABLE 4

Plasma cholesteryl ester results

| | Median concentration in µmol/l (Q1, Q3) | | | Median percentage of CE (Q1, Q3) | | |
|---|---|---|---|---|---|---|
| | No CAD | CAD | p value | No CAD | CAD | p value |
| 16:0 | 449.4 (375.3, 489.0) | 440.4 (379.0, 547.9) | 0.52 | 10.2 (9.4, 11.1) | 9.6 (8.6, 10.4) | 0.0066 |
| 16:1 | 112.1 (85.1, 156.0) | 150.5 (118.8, 214.8) | 0.0007 | 2.8 (2.2, 3.5) | 3.3 (2.6, 4.2) | 0.0128 |
| 18:0 | 58.2 (45.2, 64.8) | 66.9 (45.8, 85.0) | 0.0641 | 1.3 (1.1, 1.5) | 1.4 (1.0, 1.7) | 0.41 |
| 18:1 | 645.8 (568.4, 767.4) | 791.4 (648.7, 939.8) | 0.0016 | 15.8 (14.1, 17.0) | 16.2 (15.0, 17.7) | 0.0879 |
| 18:2 | 2421.3 (2108.2, 2733.6) | 2657.5 (2195.6, 3049.0) | 0.0674 | 56.3 (51.4, 59.2) | 54.6 (51.3, 58.0) | 0.0766 |
| 18:3 | 81.6 (64.8, 106.4) | 111.2 (90.3, 146.4) | 0.0002 | 1.9 (1.6, 2.3) | 2.3 (2.1, 2.6) | 0.0014 |
| 20:4 | 425.6 (359.5, 515.0) | 474.8 (404.7, 615.8) | 0.0166 | 10.3 (8.9, 12.0) | 10.8 (9.3, 12.8) | 0.2264 |
| 20:5 | 34.1 (27.9, 47.4) | 41.2 (33.1, 62.5) | 0.0256 | 0.9 (0.7, 1.1) | 0.9 (0.7, 1.2) | 0.50 |
| 22:6 | 19.8 (15.7, 26.1) | 22.6 (17.5, 31.1) | 0.0402 | 0.5 (0.4, 0.6) | 0.5 (0.4, 0.6) | 0.32 |
| Sum (16:1, 18:1) | 775.5 (669.3, 937.4) | 945.5 (757.5, 1106.6) | 0.0012 | 18.4 (16.0, 21.0) | 19.3 (17.8, 22.1) | 0.0354 |

Comparisons were conducted using a Kruskal-Wallis Test;
Q1 = first quartile;
Q3 = third quartile;
CAD = coronary artery disease;
For all analyses, p <= .05 denotes statistical significance, with no adjustment for the multiple comparisons.

Figure 3:
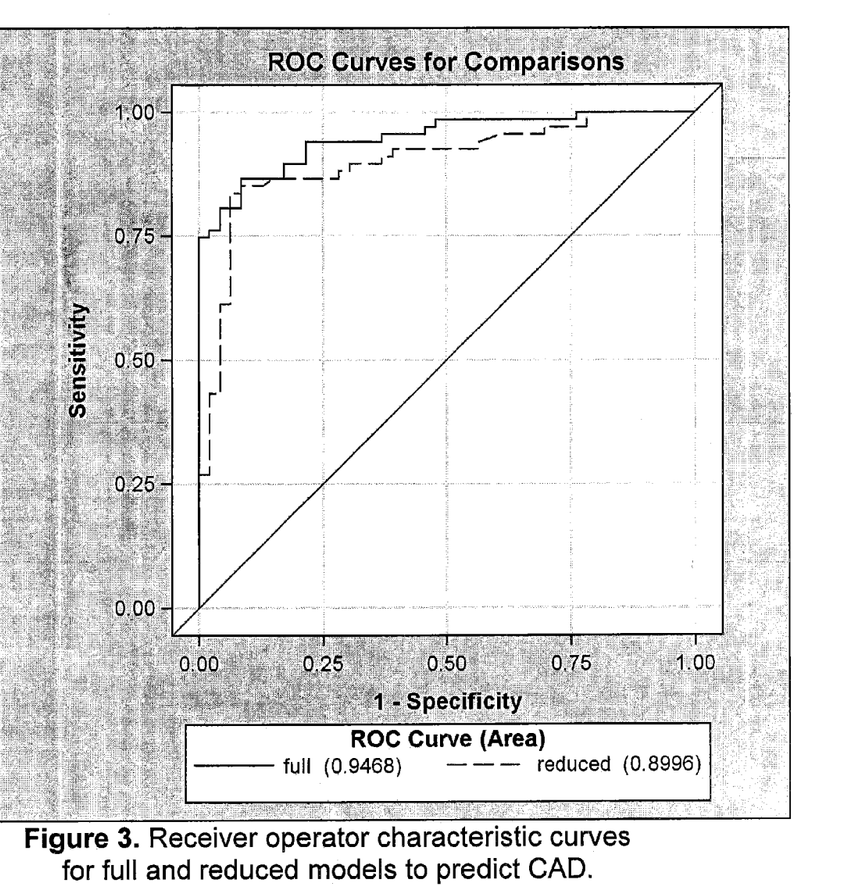
FIG. 3. Receiver operator characteristic curves for full (CE, age, gender, number of conventional risk factors) and reduced (full model minus CE) models to predict any CAD among the entire study cohort. The full model has a significantly higher C statistic, p=0.0219.

In logistic regression modeling using participants with complete data (n=113), the absolute concentration of sum CE (16:1 and 18:1) was predictive of any coronary stenosis in the final model also containing age, gender, and number of conventional coronary risk factors (AUC 0.95, 95% CI 0.91-0.98). In this model, each 10 micromolar increase in concentration was associated with a 6.5% increase in the odds of having coronary stenosis (p<0.001). No interaction terms were found to be additive to the explanatory value of the model. The Hosmer-Lemeshow goodness of fit test ($x^2_{(8)}$=13.9, p=0.08) provided no reason to reject the primary model on the basis of fit. To determine the contribution of sum CE (16:1 and 18:1) to the model, ROC curves were created and are shown in FIG. 3 for the model with and without sum CE (16:1 and 18:1). The model without sum CE (16:1 and 18:1) had a significant reduction in the C statistic to 0.89 (95% CI 0.81-0.94, p for comparison 0.004). The estimated integrated discrimination improvement from adding sum CE (16:1 and 18:1) was 0.15 (p<0.001) suggesting the sum CE adds to the ability of the model to discriminate between those with and without CAD.

The performance of the final model for CAD was then compared to the Diamond Forrester risk stratification framework in the subgroup of low risk observation unit patients with complete data for this calculation (n=58). When compared, the clinical model had superior performance based on an estimated IDI (0.403, p<0.001) indicating that the final model for CAD had better discriminatory ability. In low risk patients with serial negative troponin results (n=64), implementing a 50% predicted probability threshold to determine the need for further testing after serial cardiac markers would have led to a calculated maximum post-test probability of 1% based on the prevalence of ACS after excluding MI of 2%[10] (2%*50%=1.0%). At this threshold, 42/64 (66%) patients would have been considered negative; 1 had maximal stenosis of 50%, none with 30-day ACS. A 50% predicted probability threshold would have resulted in 22/64 (34%) patients with positive results, 8 had maximal stenosis ≥50% and none had 30-day ACS.

Exploratory analyses demonstrated that when modeling significant coronary stenosis, the variables in the final model were unchanged (AUC 0.89). In this model, each 10 micromolar increase in concentration of the sum (16:1, 18:1) was associated with a 3.5% increase in the odds for having significant stenosis (p=0.001).

When restricting the analysis to the low risk subgroup, the sum (16:1, 18:1) was similarly predictive. The final model for any coronary stenosis also contained age and gender (AUC 0.90). In this model, each 10 micromolar increase in the sum (16:1, 18:1) was associated with an increase in odds of any stenosis of 6.5% (p=0.001). The final model for significant coronary stenosis only included age and the predictor (AUC 0.89). In this model, each 10 micromolar increase in the sum (16:1, 18:1) was associated with a 4.2% increase in the odds for significant coronary stenosis (p=0.003).

In the analysis including the sum (16:1, 18:1, 18:3, 20:4, 20:5, and 22:6) as the predictor, there was no improvement in AUC of the models or the value of the predictor to the model compared to the simpler sum (16:1, 18:1) predictor. In no models were any interaction terms found to be significant. Models for each outcome and each set of predictors are as follows:

Model 1: Entire study cohort, outcome = Any coronary disease, primary predictor = sum (16:1, 18:1)

| Logistic regression | | | | Number of obs = 113 | | |
|---|---|---|---|---|---|---|
| | | | | LR chi2(4) = 87.25 | | |
| | | | | Prob > chi2 = 0.0000 | | |
| Log likelihood = −32.735808 | | | | Pseudo R2 = 0.5713 | | |
| AUC .9468 | | | | | | |
| any_cad | Odds Ratio | Std. Err. | z | P > \|z\| | [95% Conf. Interval] | |
| Sum (16:1, 18:1) | 1.006534 | .0018363 | 3.57 | 0.000 | 1.002941 | 1.010139 |
| age | 1.241218 | .0614904 | 4.36 | 0.000 | 1.126365 | 1.367782 |

-continued

Model 1: Entire study cohort, outcome = Any coronary disease, primary predictor = sum (16:1, 18:1)

| | | | | | | |
|---|---|---|---|---|---|---|
| male | 9.436404 | 7.676202 | 2.76 | 0.006 | 1.915942 | 46.47621 |
| Number risk factors | 1.997805 | .6365916 | 2.17 | 0.030 | 1.069846 | 3.730651 |

Model 2: Observation subgroup, outcome = any coronary disease, primary predictor = sum (16:1, 18:1)

| Logistic regression | Number of obs = 62 |
|---|---|
| | LR chi2(3) = 37.09 |
| | Prob > chi2 = 0.0000 |
| Log likelihood = −21.779809 | Pseudo R2 = 0.4599 |
| auc = 0.9034 | |

| any_cad | Odds Ratio | Std. Err. | z | P > \|z\| | [95% Conf. Interval] | |
|---|---|---|---|---|---|---|
| Sum (16:1, 18:1) | 1.006468 | .0019305 | 3.36 | 0.001 | 1.002692 | 1.010259 |
| age | 1.200838 | .0781986 | 2.81 | 0.005 | 1.05695 | 1.364315 |
| male | 4.865638 | 4.332211 | 1.78 | 0.076 | .8496828 | 27.86268 |

Model 3: Entire study cohort, outcome = significant coronary disease, primary predictor = sum (16:1, 18:1)

| Logistic regression | Number of obs = 113 |
|---|---|
| | LR chi2(4) = 62.96 |
| | Prob > chi2 = 0.0000 |
| Log likelihood = −45.848868 | Pseudo R2 = 0.4071 |
| AUC = 0.8938 | |

| sig_cad | Odds Ratio | Std. Err. | z | P > \|z\| | [95% Conf. Interval] | |
|---|---|---|---|---|---|---|
| Sum (16:1, 18:1) | 1.00354 | .0010197 | 3.48 | 0.001 | 1.001544 | 1.005541 |
| age | 1.154613 | .0393228 | 4.22 | 0.000 | 1.080057 | 1.234314 |
| male | 3.718503 | 2.210141 | 2.21 | 0.027 | 1.159966 | 11.92041 |
| Number risk factors | 1.712414 | .4172931 | 2.21 | 0.027 | 1.062141 | 2.760804 |

Model 4: Observation subgroup, outcome = significant coronary disease, primary predictor = sum (16:1, 18:1)

| Logistic regression | Number of obs = 62 |
|---|---|
| | LR chi2(2) = 19.31 |
| | Prob > chi2 = 0.0001 |
| Log likelihood = −17.737305 | Pseudo R2 = 0.3525 |
| AUC = 0.8885 | |

| sig_cad | Odds Ratio | Std. Err. | z | P > \|z\| | [95% Conf. Interval] | |
|---|---|---|---|---|---|---|
| Sum (16:1, 18:1) | 1.004249 | .0014328 | 2.97 | 0.003 | 1.001445 | 1.007061 |
| age | 1.171344 | .0827606 | 2.24 | 0.025 | 1.019866 | 1.34532 |

Model 5: Entire study cohort, outcome = significant coronary disease, primary predictor = sum (16:1, 18:1, 18:3, 20:4, 20:5, 22:6)

| Logistic regression | Number of obs = 113 |
|---|---|
| | LR chi2(5) = 68.35 |
| | Prob > chi2 = 0.0000 |
| Log likelihood = −43.151639 | Pseudo R2 = 0.4420 |
| AUC = 0.9056 | |

| sig_cad | Odds Ratio | Std. Err. | z | P > \|z\| | [95% Conf. Interval] | |
|---|---|---|---|---|---|---|
| Sum (significant CE) | 1.002624 | .0007152 | 3.67 | 0.000 | 1.001223 | 1.004027 |
| age | 1.154735 | .0419362 | 3.96 | 0.000 | 1.075399 | 1.239924 |
| white | 4.364957 | 3.267844 | 1.97 | 0.049 | 1.006293 | 18.93371 |

-continued

Model 5: Entire study cohort, outcome = significant coronary disease, primary predictor = sum (16:1, 18:1, 18:3, 20:4, 20:5, 22:6)

| | | | | | | |
|---|---|---|---|---|---|---|
| male | 4.051486 | 2.613006 | 2.17 | 0.030 | 1.144542 | 14.34158 |
| framingham | 1.69183 | .4264504 | 2.09 | 0.037 | 1.032283 | 2.772774 |

Model 6: Observation subgroup, outcome = significant coronary disease, primary predictor = sum (16:1, 18:1, 18:3, 20:4, 20:5, 22:6)

| Logistic regression | | | | Number of obs = 62 | | |
|---|---|---|---|---|---|---|
| | | | | LR chi2(2) = 19.58 | | |
| | | | | Prob > chi2 = 0.0001 | | |
| Log likelihood = −17.602642 | | | | Pseudo R2 = 0.3574 | | |
| AUC = 0.8827 | | | | | | |

| sig_cad | Odds Ratio | Std. Err. | z | P > \|z\| | [95% Conf. Interval] | |
|---|---|---|---|---|---|---|
| Sum (significant CE) | 1.002625 | .0009186 | 2.86 | 0.004 | 1.000826 | 1.004427 |
| age | 1.178033 | .0876034 | 2.20 | 0.028 | 1.01826 | 1.362876 | ln(Probability any stenosis/1−probability any stenosis)=−17.2+0.692(number of risk factors)+ 0.0065(concentration CE 16:1+concentration 18:1)+0.216(age)+1.12(gender*)    Formula for model 1

*gender=1 if male, 2 if female ln(Probability significant stenosis/1−probability significant stenosis)=−11.97+0.538(number of risk factors)+0.0035(concentration CE 16:1+concentration 18:1)+0.144(age)+0.657(gender*)    Formula for model 3

*gender=1 if male, 2 if female

III. Discussion.

The results of this analysis suggest that plasma concentrations of cholesteryl esters, the synthesis of which was predominately catalyzed via ACAT2 are associated with coronary stenosis in patients with acute chest pain. The association was significant when examined in the entire study cohort consisting of patients with a wide spectrum of disease severity, and remained significant when restricting the analysis to the subgroup of emergency department patients with low-risk chest pain.

The background information suggesting that cholesteryl ester composition might matter in coronary artery atherosclerosis comes from numerous studies done in animal models and in humans: Perhaps the first observations to directly establish a link came in 1997 when it was shown that the cholesteryl ester secretion rate from livers in isolated perfusion was predictive of the extent of coronary artery atherosclerosis in the liver donor monkeys. (9) The acyl composition for cholesteryl esters made by the tissue esterifying enzyme ACAT was predominantly oleate, and percentage of this CE was enhanced when the diet was enriched in oleate. The plasma enzyme LCAT contributes mostly cholesteryl linoleate. Subsequent studies in ARIC (21) and in Sweden (22) have confirmed that in humans, plasma cholesteryl oleate is positively associated with carotid intimal medial thickness or mortality from Cardiovascular disease, respectively. Numerous studies in genetically engineered mice lacking the enzyme ACAT2 have also showed that marked reductions in cholesteryl oleate in plasma LDL occur together with reduced aortic atherosclerosis when ACAT2 is absent (23). Thus, a convincing picture is available that a higher percentage of cholesteryl oleate in plasma LDL cholesteryl esters is consistently associated with increased atherosclerosis.

In order to be useful as a biomarker, CE measurements have to be obtainable. The measurements in this analysis were conducted in a research lab using a mass spectrometer. These instruments are relatively expensive but multiplexing an instrument use for more than one type of analyses would substantially reduce sample cost. Technical expertise would require an individual that can dilute 5 to 10 µL of plasma or blood into a fixed volume of solvent. Mass spectrometer upkeep would require a service contract and an individual that could tune and check the instrument daily. Since most academic institutions have one or more mass spectrometer facilities, establishing this sort of facility would be feasible. A typical cost for sample analysis in an academic mass spectrometer facility is on the order of $30. If a modern electrospray mass spectrometer is installed the turn-around time would be minimal, 0.5-1 h.

There exists a substantial need for more refined risk stratification schemes to guide the evaluation of patients with acute chest pain. Existing clinical decision rules comprised of combinations of traditional risk factors, biomarkers of necrosis and clinical variables have proven insufficiently sensitive to exclude ACS. (13, 24, 25) Further, conventional risk factors for atherosclerosis have not proven useful when evaluating patients with acute chest pain. (2, 6) In distinction with prior efforts, we have chosen not to predict ACS, but rather to predict coronary stenosis. ACS consists of MI and unstable angina, both of which are most commonly the result of coronary atherosclerotic disease. MI, by definition, is excluded with serial cardiac markers of necrosis. In contrast, unstable angina is defined by non-elevated markers of necrosis and requires cardiac imaging for proper diagnosis. Reducing the need for cardiac imaging could improve health by reducing exposure to ionizing radiation using in the diagnostic testing process and could improve healthcare efficiency by reducing the number of unnecessary imaging tests. Therefore, predicting a precursor for unstable angina, coronary atherosclerotic disease, could improve health and increase healthcare efficiency. It should be noted that this approach could miss the relatively rare secondary causes of ACS if they are not associated with myocardial necrosis, such as de-novo coronary thrombosis, coronary embolism, or coronary vasospasm.

The most clinically useful model in our analysis appears to be the sum of the plasma concentrations of CE 16:1 and CE 18:1, combined with age, gender, and the number of traditional coronary risk factors to predict the presence of any coronary atherosclerosis in low risk patients. If validation of this model were successful, this measure could be used to determine the need for coronary imaging or stress testing after the exclusion of MI. Our first examination in our low risk subgroup suggests that this approach could result in a meaningful reduction in imaging. Further prospective investigations should validate these findings, evaluate the potential clinical utility, refine appropriate cut-points, and examine model calibration.

REFERENCES

1. Pitts S R, Niska R W, Xu J, Burt C W. National Hospital Ambulatory Medical Care Survey: 2006 emergency department summary. National health statistics reports; no 7. Hyattsville, Md.: National Center for Health Statistics. 2008.
2. Anderson J L A C, Antman E M, Bridges C R, Califf R M, Casey D E Jr, Chavey W E II, Fesmire F M, Hochman J S, Levin T N, Lincoff A M P E, Theroux P, Wenger N K, Wright R S. ACC/AHA 2007 guidelines for the management of patients with unstable angina/non-ST-elevation myocardial infarction: a report of the American College of Cardiology/American Heart Association Task Force on Practice Guidelines (Writing Committee to Revise the 2002 Guidelines for the Management of Patients With Unstable Angina/Non-ST-Elevation Myocardial Infarction). Circulation 2007; 116:e148-304.
3. Smith S C, Jr, Allen J, Blair S N, et al. AHA/ACC Guidelines for Secondary Prevention for Patients With Coronary and Other Atherosclerotic Vascular Disease: 2006 Update: Endorsed by the National Heart, Lung, and Blood Institute 10.1161/CIRCULATION-AHA.106.174516. Circulation 2006; 113:2363-2372.
4. D'Agostino R B, Sr., Grundy S, Sullivan L M, Wilson P. Validation of the Framingham coronary heart disease prediction scores: results of a multiple ethnic groups investigation. Jama 2001; 286:180-187.
5. Grundy S M, Balady G J, Criqui M H, et al. Primary Prevention of Coronary Heart Disease: Guidance From Framingham: A Statement for Healthcare Professionals From the AHA Task Force on Risk Reduction. Circulation 1998; 97:1876-1887.
6. Han J H, Lindsell C J, Storrow A B, et al. The role of cardiac risk factor burden in diagnosing acute coronary syndromes in the emergency department setting. Ann Emerg Med 2007; 49:145-152, 152 e141.
7. Lee R G, Kelley K L, Sawyer J K, Farese R V, Jr., Parks J S, Rudel L L. Plasma cholesteryl esters provided by lecithin:cholesterol acyltransferase and acyl-coenzyme a: cholesterol acyltransferase 2 have opposite atherosclerotic potential. Circ Res 2004; 95:998-1004.
8. Willner E L, Tow B, Buhman K K, et al. Deficiency of acyl CoA:cholesterol acyltransferase 2 prevents atherosclerosis in apolipoprotein E-deficient mice. Proc Natl Acad Sci USA 2003; 100:1262-1267.
9. Rudel L L, Haines J, Sawyer J K, Shah R, Wilson M S, Carr T P. Hepatic origin of cholesteryl oleate in coronary artery atherosclerosis in African green monkeys. Enrichment by dietary monounsaturated fat. J Clin Invest 1997; 100:74-83.
10. Öhrvall M, Berglund L, Salminen I, Lithell H, Aro A, Vessby B. The serum cholesterol ester fatty acid composition but not the serum concentration of alpha tocopherol predicts the development of myocardial infarction in 50-year-old men: 19 years follow-up. Atherosclerosis 1996; 127:65-71.
11. Anderson J L, Adams C D, Antman E M, et al. ACC/AHA 2007 Guidelines for the Management of Patients With Unstable Angina/Non ST-Elevation Myocardial Infarction. A Report of the American College of Cardiology/American Heart Association Task Force on Practice Guidelines (Writing Committee to Revise the 2002 Guidelines for the Management of Patients With Unstable Angina/Non ST-Elevation Myocardial Infarction). Circulation 2007.
12. Antman E M, Cohen M, Bernink P J L M, et al. The TIMI Risk Score for Unstable Angina/Non-ST Elevation MI: A Method for Prognostication and Therapeutic Decision Making. JAMA 2000; 284:835-842.
13. Pollack C V, Jr., Sites F D, Shofer F S, Sease K L, Hollander J E. Application of the TIMI risk score for unstable angina and non-ST elevation acute coronary syndrome to an unselected emergency department chest pain population. Acad Emerg Med 2006; 13:13-18.
14. Hollander J E, Blomkalns A L, Brogan G X, et al. Standardized reporting guidelines for studies evaluating risk stratification of ED patients with potential acute coronary syndromes. Acad Emerg Med 2004; 11:1331-1340.
15. Thomas J D, Zoghbi W A, Beller G A, et al. ACCF 2008 Training Statement on Multimodality Noninvasive Cardiovascular Imaging A Report of the American College of Cardiology Foundation/American Heart Association/American College of Physicians Task Force on Clinical Competence and Training Developed in Collaboration With the American Society of Echocardiography, the American Society of Nuclear Cardiology, the Society of Cardiovascular Computed Tomography, the Society for Cardiovascular Magnetic Resonance, and the Society for Vascular Medicine. J Am Coll Cardiol 2009; 53:125-146.
16. Garber D W, Kulkarni K R, Anantharamaiah G M. A sensitive and convenient method for lipoprotein profile analysis of individual mouse plasma samples. J Lipid Res 2000; 41:1020-1026.
17. Allain C C, Poon L S, Chan C S, Richmond W, Fu P C. Enzymatic determination of total serum cholesterol. Clin Chem 1974; 20:470-475.
18. Fossati P, Prencipe L. Serum triglycerides determined colorimetrically with an enzyme that produces hydrogen peroxide. Clin Chem 1982; 28:2077-2080.
19. Royston P, Altman D G. Regression using fractional polynomials of continuous covariates: parsimonious parametric modeling. Applied Statistics 1994; 43:3, 429-467.
20. Austen W G, Edwards J E, Frye R L, et al. A reporting system on patients evaluated for coronary artery disease. Report of the Ad Hoc Committee for Grading of Coronary Artery Disease, Council on Cardiovascular Surgery, American Heart Association. Circulation 1975; 51:5-40.
21. Ma J, Folsom A, Lewis L, Eckfeldt J. Relation of plasma phospholipid and cholesterol ester fatty acid composition to carotid artery intima-media thickness: the Atherosclerosis Risk in Communities (ARIC) Study The American Journal of Clinical Nutrition 1997 65 551-559
22. Warensjo E, Sundstrom J, Vessby B, Cederholm T, Riserus U. Markers of dietary fat quality and fatty acid desaturation as predictors of total and cardiovascular mortality: a population-based prospective study. Am J Clin Nutr 2008; 88:203-209.
23. Bell T A, 3rd, Kelley K, Wilson M D, Sawyer J K, Rudel L L. Dietary fat-induced alterations in atherosclerosis are 24. Limkakeng A, Jr., Gibler W B, Pollack C, et al. Combination of Goldman risk and initial cardiac troponin I for emergency department chest pain patient risk stratification. Acad Emerg Med 2001; 8:696-702.
25. Marsan R J, Jr., Shaver K J, Sease K L, Shofer F S, Sites F D, Hollander J E. Evaluation of a Clinical Decision Rule for Young Adult Patients with Chest Pain. Acad Emerg Med 2005; 12:26-31.
26. Meijboom W B, Meijs M F, Schuijf J D, et al. Diagnostic accuracy of 64-slice computed tomography coronary angiography: a prospective, multicenter, multivendor study. J Am Coll Cardiol 2008; 52:2135-2144.
27. Budoff M J, Dowe D, Jollis J G, et al. Diagnostic Performance of 64-Multidetector Row Coronary Computed Tomographic Angiography for Evaluation of Coronary Artery Stenosis in Individuals Without Known Coronary Artery Disease: Results From the Prospective Multicenter ACCURACY (Assessment by Coronary Computed Tomographic Angiography of Individuals Undergoing Invasive Coronary Angiography) Trial. Journal of the American College of Cardiology 2008; 52:1724-1732.

That which is claimed is:

1. A method for determining a prediction of risk and/or an indication of extent of coronary stenosis in a human subject, said method comprising the steps of:
    determining a level of at least one cholesteryl ester selected from the group consisting of: cholesteryl palmitate (CE 16:0), cholesteryl palmitoleate (CE 16:1), cholesteryl stearate (CE 18:0), cholesteryl oleate (CE 18:1), cholesteryl linoleate (CE 18:2), cholesteryl linolenate (CE 18:3), cholesteryl arachidonate (CE 20:4), cholesteryl eicosapentenoate (CE 20:5), cholesteryl docosapentaenoate (CE 22:5), cholesteryl docosahexanoate (CE 22:6), and combinations thereof in a blood sample from said subject; and
    correlating said level of CE 16:0, CE 16:1, CE 18:0, CE 18:1, CE 18:2, CE 18:3, CE 20:4, CE 20:5, CE 22:5, CE 22:6, or combinations thereof, with a control, thereby providing a prediction of risk and/or indication of extent of coronary stenosis in said subject.

2. The method of claim 1, further comprising the step of:
    adjusting the prediction of risk and/or the indication of extent of coronary stenosis in view of the age and/or gender of said subject.

3. The method of claim 1, wherein said subject is afflicted with acute chest pain.

4. The method of claim 3, wherein said coronary stenosis is significant coronary stenosis.

5. The method of claim 1, wherein said subject is not afflicted with acute chest pain.

6. The method of claim 5, wherein said coronary stenosis is moderate coronary stenosis.

7. The method of claim 1, wherein said cholesteryl ester comprises CE 16:1 and CE 18:1 in combination.

8. The method of claim 1, wherein said blood sample is selected from the group consisting of blood serum, blood plasma, and whole blood.

9. The method of claim 1, further comprising:
    determining the level of said at least one cholesteryl ester in said blood sample by mass spectrometry.

10. A computer-based method for determining a prediction of risk and/or an indication of extent of coronary stenosis in a human subject, said method comprising the steps of:
    (a) inputting the level of at least one cholesteryl ester measured in a blood sample collected from said subject, wherein the at least one cholesteryl ester is selected from the group consisting of: cholesteryl palmitate (CE 16:0), cholesteryl palmitoleate (CE 16:1), cholesteryl stearate (CE 18:0), cholesteryl oleate (CE 18:1), cholesteryl linoleate (CE 18:2), cholesteryl linolenate (CE 18:3), cholesteryl arachidonate (CE 20:4), cholesteryl eicosapentenoate (CE 20:5), cholesteryl docosapentaenoate (CE 22:5), cholesteryl docosahexanoate (CE 22:6), and combinations thereof; and
    (b) inputting the age and gender of said subject; and then
    (c) generating from said cholesteryl ester level, said age and said gender a prediction of risk and/or an indication of extent of coronary stenosis in said subject.

11. The method of claim 10, further comprising the step of:
    inputting the presence or absence of at least one additional risk factor in said subject;
    and wherein said generating step further comprises generating from said cholesteryl ester level, said age, and said at least one additional risk factor a prediction of risk and/or indication of extent of coronary stenosis in said subject.

12. The method of claim 11, wherein said at least one additional risk factor comprises at least three additional risk factors.

13. The method of claim 11, wherein said at least one additional risk factor is selected from the group consisting of hyperlipidemia, smoking, diabetes, hypertension, obesity, substance abuse, sedentary lifestyle, and family history.

14. The method of claim 10, wherein said subject is afflicted with acute chest pain.

15. The method of claim 14, wherein said coronary stenosis is significant coronary stenosis.

16. The method of claim 10, wherein said subject is not afflicted with acute chest pain.

17. The method of claim 16, wherein said coronary stenosis is moderate coronary stenosis.

18. The method of claim 10, wherein said cholesteryl ester comprises CE 16:1 and CE 18:1 in combination.

19. The method of claim 10, wherein said blood sample is selected from the group consisting of blood serum, blood plasma, and whole blood.

20. The method of claim 10, wherein said generating step is carried out with an empirically-based model of actual clinical experience.

21. The method of claim 10, wherein said generating step is carried out with a regression model.

22. The method of claim 10, further comprising:
    determining the level of said at least one cholesteryl ester in said blood sample by mass spectrometry.

* * * * *

UNITED STATES PATENT AND TRADEMARK OFFICE
CERTIFICATE OF CORRECTION

PATENT NO. : 9,726,683 B2
APPLICATION NO. : 14/948938
DATED : August 8, 2017
INVENTOR(S) : Rudel et al.

Page 1 of 1

It is certified that error appears in the above-identified patent and that said Letters Patent is hereby corrected as shown below:

On the Title Page (57) Abstract: Please delete abstract in it's entirety and replace it with the following:
-- The present invention is directed to methods for prediction of risk and/or indication of extent of coronary stenosis or atherosclerosis in human subjects using cholesteryl ester levels. --

In the Specification

Column 1, Field of The Invention: Please delete the Field Of The Invention in its entirety and replace it with the following:
-- The present invention concerns devices, systems, computer-based methods and methods for generating a prediction of risk and/or indication of extent of coronary stenosis or atherosclerosis in human subjects, for diagnostic purposes in subjects who are afflicted with chest pain or symptoms concerning for acute coronary syndrome, as well as for prognostic purposes in subjects who are not afflicted with chest pain. --

Signed and Sealed this
Twenty-first Day of August, 2018

Andrei Iancu
*Director of the United States Patent and Trademark Office*